United States Patent [19]

Tsao et al.

[11] Patent Number: 4,812,173

[45] Date of Patent: Mar. 14, 1989

[54] STABILIZED HYDROGEN PEROXIDE CONTACT LENS DISINFECTING SOLUTION

[75] Inventors: Fu-Pao Tsao, Lawrenceville; M. Alicja Sills, Norcross, both of Ga.

[73] Assignee: Ciba-Geigy Corporation, Ardsley, N.Y.

[21] Appl. No.: 45,094

[22] Filed: May 1, 1987

[51] Int. Cl.$^4$ ............................................... A61L 2/18
[52] U.S. Cl. .......................................... 134/27; 134/2; 134/3; 134/42; 252/106; 252/186.29; 423/272; 423/273
[58] Field of Search ........................ 134/2, 3, 27, 42; 423/272, 273; 252/106, 186.29

[56] References Cited

U.S. PATENT DOCUMENTS

| | | | |
|---|---|---|---|
| 3,122,417 | 2/1964 | Blaser et al. | 423/272 |
| 3,345,225 | 10/1967 | Lacal | 134/28 |
| 3,687,627 | 8/1972 | Stalter | 423/273 |
| 3,905,907 | 9/1975 | Shiga | 134/3 |
| 4,110,242 | 8/1978 | Hase et al. | 423/273 |
| 4,585,488 | 4/1986 | Giefer | 134/32 |

*Primary Examiner*—John Doll
*Assistant Examiner*—Wayne A. Langel
*Attorney, Agent, or Firm*—Irving M. Fishman

[57] ABSTRACT

Stabilized hydrogen peroxide disinfecting solutions containing diphosphonic acids (such as hydroxyethylidene diphosphonic acid), and glycerin are disclosed along with a disinfection method.

9 Claims, No Drawings

STABILIZED HYDROGEN PEROXIDE CONTACT LENS DISINFECTING SOLUTION

FIELD OF THE INVENTION

The invention relates to disinfecting solutions used primarily with contact lenses, especially soft contact lenses, and disinfecting methods employing such solutions.

BACKGROUND OF THE INVENTION

Hydrogen peroxide solutions have been used for many years for a variety of purposes, including bleaching, disinfecting, and cleaning a variety of surfaces ranging from skin, hair, and mucous membranes to contact lenses to household and industrial surfaces and instruments. Unfortunately, unless very stringent conditions are met, hydrogen peroxide solutions begin to decompose into $O_2$ gas and water within an extremely short time. Typical hydrogen peroxide solutions in use for these purposes are in the range of from about 0.5 to about 6% by weight of hydrogen peroxide in water. The rate at which such dilute hydrogen peroxide solutions decompose will, of course, be dependent upon such factors as pH and the presence of trace amounts of various metal impurities, such as copper or chromium, which may act to catalytically decompose the same. Moreover, at moderately elevated temperatures the rate of decomposition of such dilute aqueous hydrogen peroxide solutions is greatly accelerated. Hence, hydrogen peroxide solutions which have been stabilized against peroxide breakdown are in very great demand.

A large variety of stabilizers have been proposed for use with hydrogen peroxide to deactivate trace catalytic impurities, including stannous salts, ethylene diamine tetracetic acid, and the like.

The primary hydrogen peroxide stabilizer which has been developed and in wide use today is sodium stannate. This stabilizer serves the desired function of substantially reducing hydrogen peroxide decomposition, and is suitable for a number of applications to which such solutions are put. However, sodium stannate preserved hydrogen peroxide solutions cannot be used with high water content ionic lens materials, since a hazing or milky filming of the lens material results.

In an effort to obtain stabilized peroxide solutions for use with such materials, whether as lenses or other fabricated articles, materials such as Dequest ® 2060 (diethylenetriamine penta(methylene phosphonic acid), produced by Monsanto) have been used with hydrogen peroxide.

For example, U.S. Pat. No. 3,860,391 discloses bleacing compositions containing hydrogen peroxide and, as a stabilizer, amino lower alkylene polyphosphates, including diethylene triamine penta (methylenephosphinic acid) or salts thereof, and/or hydroxy alkane phosphates, with or without additional stabilizer constituents, and adjusted to a pH of between about 9.0 and 12.0 with, e.g. sodium hydroxide, for the bleaching of cellulose materials. Exemplified are compositions having a pH of 12.0.

While Dequest ® 2060 is a good hydrogen peroxide stabilizer, it has been found that its protective action is self limiting. Those stabilizers act by chelating metals, which metals catalyze or enhance the peroxide decomposition. However, this stabilizer undergoes changes in peroxide solutions which make it a poor chelator for metals, and hence, the stabilizing effect is dissipated. It is usually added to the non-peroxide components to chelate peroxide decomposing contaminants before the peroxide is added thereto. If it is added to the peroxide portion, the nitrogens in the Dequest ® 2060 become oxidized and the chelating power is lost.

Soft contact lenses are characteristically prepared from hydrophilic polymers, such as polymers of hydroxyethyl methacrylate (HEMA), crosslinked with a conventional crosslinking agent, such as ethylene glycol dimethacrylate (EGDMA), or more complex copolymer systems including copolymers of HEMA, EGDMA, methacrylic acid and/or poly-N-vinylpyrrolidone, and the like. Other hydrophilic monomers conventionally employed in varying amounts in the manufacture of soft contact lenses include, for example, N-vinylpyrrolidone, glyceryl methacrylate, diethylene glycol monomethacrylate, triethylene glycol monomethacrylate, allyl 2-hydroxyethyl ether, acrylic acid, acrylamide, N,N-dimethylacrylamide, and the like. Other conventional crosslinking agents commonly employed include, inter alia, diallyl ether, divinyl benzene, diethylene glycol dimethacrylate, triethylene glycol dimethacrylate, diallyl succinate, allyl methacrylate, glycerin tri-methacrylate, and the like. Moreover, various amounts of relatively hydrophobic monomer units can be employed in the manufacture of soft contact lens materials, as long as the final copolymer network exhibits the desired hydrophilic characteristics. Typical hydrophobic monomers include methyl methacrylate, glycidyl methacrylate, N-(1,1-dimethyl- 3-oxobutyl)acrylamide, siloxane methacrylates, perfluoroalkyl methacrylates, perfluoroalkoxyperfluoroalkyl methacrylates, and the like. In general, such lenses exhibit marked hydrophilic properties and, when wet, absorb water and are soft and flexible.

While these lenses are not actually perforate, they do have a sufficient degree of molecular porosity to permit water, oxygen and tear fluids to permeate the lens structure. In order for the disinfection of such lenses to be effective after they have been worn, it is important that contaminants be removed from both surfaces, and the interior of the lens, to the extent contaminants are present therein. Hydrogen peroxide in the form of a dilute solution, e.g. about 0.5 to 6% by weight in water, is known to be effective for use with contact lenses in order to kill any contaminating microorganisms.

Unfortunately, the highly basic compositions indicated above are undesirable in a contact lens environment, especially in the disinfection of contact lenses, and in uses of hydrogen peroxide where the composition directly contacts skin, mucous membranes, or instruments made of contact lens polymer materials and subsequently are used on or in the body.

The above difficulties and growing importance of peroxide as a disinfectant for contact lens materials makes it imperative that a suitable peroxide stabilizer be found.

OBJECTS OF THE INVENTION

One object of this invention is to provide stabilizers for hydrogen peroxide solutions which are compatible with contact lens materials (whether fabricated into contact lenses or other articles) free from the above-mentioned disadvantages.

Another object of the invention is to provide a stabilized hydrogen peroxide solution for use with high water content ionic lens materials.

A further object of the invention is to provide a stabilized hydrogen peroxide solution having a stabilizer which does not tend to lose its stabilizing ability upon exposure to hydrogen peroxide.

A still further object is to provide a method of disinfecting contact lens materials and other articles fabricated from such materials with a stabilized hydrogen peroxide solution.

SUMMARY OF THE INVENTION

Surprisingly, the foregoing objects and others are achieved by a composition of water, hydrogen peroxide, a primary peroxide stabilizer of the formula

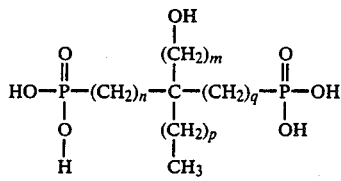

or a physiologically compatible salt thereof and a secondary peroxide stabilizer selected from glycerine, polyvinyl alcohol, propylene glycol, polyacrylic acid, diethylene glycol, and sodium hexametaphosphate sodium polyphosphate.

DETAILED DESCRIPTION OF THE INVENTION

The instant invention is a hydrogen peroxide disinfecting solution, primarily for disinfecting contact lens materials, especially when such materials are in the form of contact lenses. The invention is of particular importance to the disinfection of high water content, especially ionic, contact lens materials, most importantly to disinfecting such materials having a water content in excess of about 30%, even more importantly to such materials and expecially contact lenses with a water content in the range of about 40% to about 80%. The invention is also of great importance regarding disinfection of any lens or lens material which is heat sensitive and therefore cannot be subjected to heat sterilization. Of course, any lens material (and other materials generally which are stable to hydrogen proxide) which can be heat treated for disinfection can also be disinfected with the instant invention.

The solution of the invention contains hydrogen peroxide in a concentration which is suitable for disinfecting puposes, preferably about 0.5% to about 6%, more preferably about 2% to about 6% by weight, most preferably about 3% by weight. In addition to hydrogen peroxide, the solution contains a primary peroxide stabilizer selected from diphosphonic acid alkanols of the formula

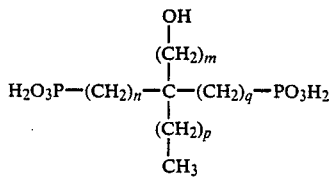

wherein each of n, m, p and q is independently 0–4, preferably 0 or 1, most preferably 0, or a physiologically compatible salt thereof. The compound wherein each n, m, p and q is zero is manufactured by Monsanto under the name Dequest ® 2010. The solution further contains a secondary peroxide stabilizer selected from glycerin, polyvinyl alcohol having a molecular weight in the range of about 5,000 to about 150,000 (as long as water soluble) and being at least 80% hydrolized, propylene glycol, polyacrylic acid having a molecular weight of about 2,000 to about 100,000, diethylene glycol, and sodium hexametaphosphate sodium polyphosphate (available from FMC under the name Hexaphos ®).

The primary stabilizer is present per 100 g of solution in an amount of at least about 0.024 m mole (50 ppm), preferably 0.039 m mole (80 ppm) up to about 0.34 m mole (700 ppm) more preferably 0.049 m mole (100 ppm) up to about 0.29 m mole (600 ppm), most preferably 0.073 m mole (150 ppm) to about 0.19 m mole (400 ppm). The amounts in parentheses are for Dequest ® 2010 which has a molecular weight of 206. Other primary stabilizers should be present in molar equivalents thereto.

The secondary stabilizer is present in an amount of at least 0.054 m mole (50 ppm), preferably 0.087 m mole (80 ppm) to about 1.09 m mole (1000 ppm), more preferably from about 0.109 m mole (100 ppm) to about 0.87 m mole (800 ppm), most preferably about 0.22 m mole (200 ppm) to about 0.65 m mole (600 ppm). The quantities in parentheses apply to glycerin (molecular weight=92); when other secondary stabilizers are used, approximately equimolar amounts thereto are indicated.

The pH of the solution can vary over a wide range but preferably is between about 5.5 and 8.0, more preferably between about 6.0 and about 7.5, still more preferably between about 6.2 and about 7.4. The pH may be adjusted within these bounds, if desired, by any conventional occularly acceptable buffering system or compound.

Physiologically compatible salts of the diphosphonic acid alkanols include, for example, water soluble salts with conventional pharmaceutically acceptable cationic moieties, including the alkali metal, alkaline earth metal, ammonium and amine cations. Suitable amine salts include, for example, mono-, di- and tri-lower alkyl amines, such as methylamine, ethylamine, diethylamine, triethylamine, dimethylamine, trimethylamine, propylamine, and the like; and mono-, di- and tri- lower hydroxyalkyl amines, such as ethanolamine, diethanolamine, triethanolamine, glucamine, 2-hydroxypropylamine, and the like.

By "lower" in the context of an alkyl group is meant up to 6 carbon atoms, preferably up to 4 carbon atoms.

If desired, additional conventional stabilizers may be employed in conjunction with the primary and secondary stabilizers mentioned above, provided that they do not suffer from the "clouding or filming" defect mentioned above. Hence, stannate stabilizers are specifically excluded from formulations which would be used to disinfect polymer materials typically found in contact lenses. However, where the material to be disinfected is not adversely affected by stannate stabilizers, the stannates can be added if desired.

Suitable conventional stabilizers include: water soluble stannates (in accordance with the above proviso), such as an alkali metal or ammonium stannates, for example sodium stannate, a water soluble phosphate, polyphosphate or metaphosphate salt, such as an alkali metal or ammonium salt thereof for example diethylenetriamine penta(methylenephosphonic acid); or an amino polycarboxylic acid chelating agent, such as ethylene diamine tetraacetic acid, nitrilo triacetic acid or a water soluble salt thereof, such as an alkali metal or ammonium salt, especially the sodium salt, or mixtures thereof. Where such additional stabilizers are employed, they are general employed in a physiologically tolerable amount, e.g. in an amount of about 0.002 to about 0.1% by weight.

If desired, ophthalmologically acceptable salts can be present to increase the solution tonicity. Preferably, the solution tonicity is between 390 milliosmole and about 1,700 milliosmole, more preferably from about 420 to about 1,350 milliosmole, most preferably 420 to about 1320 milliosmole before decomposition of the peroxide, and preferably approximately 250 milliosmole to 350 milliosmole after the peroxide is decomposed. Suitable tonicity enhancing agents include, for example alkali metal halides, phosphates, hydrogen phosphates, and borates. Preferred are sodiumchloride, sodium phosphate monobasic and sodium phosphate dibasic. The function of such tonicity enhancing agents is to increase and comfort level of the solution, upon decomposition of the hydrogen peroxide during or subsequent to contact lens disinfection, which adheres to the contact lens, in the eye of the patient.

Preferably sufficient tonicity enhancing agents are present in the solution, such that, upon decomposition of the hydrogen peroxide therein, the resulting solution is substantially isotonic, e.g. substantially equivalent to a 0.9% by weight aqeuous sodium chloride solution.

A further optional ingredient is a thickener or viscosity enhancing agent. Any of the substances known in these categories which are ocularly acceptable can be used. Typical suitable thickeners include, inter alia, polyvinylalcohol, hydroxy ethylcellulose, etc. Thickeners may be present in any amount up to an amount sufficient to raise the overall solution viscosity to about 1000 cps, preferably to not more than 100 cps.

If desired, an additional ocularly acceptable disinfecting agent may be present to enhance the spectrum of the hydrogen peroxide solution disinfection properties. Such additional disinfecting agent may be present in any quantity which will not adversely affect the other components. If present, it is preferably in an amount at which it is disinfectively active up to about 2000 ppm; more preferably from about 10 ppm to about 1000 ppm.

In all cases above, ocularly acceptable materials have been indicated for use in the stabilized hydrogen peroxide solution used to disinfect contact lens materials. This is more of a safety factor than a requirement. Since the hydrogen peroxide in the solution must or should be purged from the disinfected lens and if rinsing is the mode of removal, it is possible, but not recommended, to use ocularly unacceptable components provided that rinsing will remove any residue of such component from the lens.

Furthermore, when the invention solution is being used to disinfect contact lens materials which have been fabricated into articles other than contact lenses, or when the hydrogen peroxide solution is used for bleaching purposes or photographic applications, an even greater range of the optional solution components than set out above can be used.

For example, if compatable with the elements and purpose for which the stabilized hydrogen peroxide solution is being used, one or more of the components may remain on or in the polymer network of the article which component would be incompatible with the ocular environment. The scope of such additives for these applications of the stabilized hydrogen peroxide solution will be apparent to those of ordinary skill in the art for which the solution is being applied.

Formulation of the solutions of the invention can be made in any conventional manner. For example, all of the components other than the hydrogen peroxide and water can be placed in a container and fresh, preferably concentrated, hydrogen peroxide added thereto with mixing. Alternatively the dry components can be rubbed up with a small portion of liquid secondary stabilizer, then the remainder of the secondary stabilizer added, followed by the hydrogen peroxide, and most of the water. The viscosity enhancing agent, i.e. thickener, can then be added or the formed solution can be added to the thickener. One of ordinary skill in the art will be aware of numerous variations in the manner of formulating the solutions of the invention.

Contact lenses are disinfected by the present invention by immersing the lens in the solution. The lens should remain in the solution for a period of not less than about 10 minutes, preferably from about 20 minutes to about 60 minutes. If the lens material is resistant to or stable against heat treatment, both heat and peroxide disinfection can be used. If both are utilized, the time that the lens material must be in the solution of the invention can be decreased, but if both disinfection treatments are needed, the lens material should preferably remain in the solution for no less than 10 minutes.

After the lens material has been immersed in the inventive solution for an appropriate period, the hydrogen peroxide must be removed (if a contact lens is being disinfected). Other medicinal and non medicinal uses of the material being disinfected may or may not require this step. Persons of ordinary skill in the relevant art will be aware if this step is necessary or desirable. When it is desirable to "neutralize" the peroxide activity, any means known, such as rinsing, contacting the solution with platinum, catalase, or any other substance known to decompose hydrogen peroxide, will suffice. When contact lens disinfection is involved the peroxide neutralizer should be completely removable by rinsing or be physiologically compatible. Additional physiological compatible peroxide neutralizing agents include reducing agent such as pyruvic acid and suitable salts thereof such as the sodium salt.

It should be apparent that the instant solutions stabilize hydrogen peroxide and therefore will find additional utility in any application to which hydrogen peroxide may be put. Hence, while one of the primary utilities is disinfection of contact lens materials, the full scope of the invention is the full scope of hydrogen peroxide utility.

Having fully described the invention, the following Examples, which do not limit the invention, are presented for a better understanding thereof.

EXAMPLE 1

0.010 g of glycerine are dissolved in 80 ml of purified deionized water to which 10 ml of Fisher Chemical pure grade 30% hydrogen peroxide is added. Purified deionized water is added to bring the solution to a volume of 100 ml. The pH is adjusted to 6.5 by HCl or NaOH—. Hot stability of this solution is over 95%.

Hot stability is calculated as:

$$\left[ \frac{H_2O_2 \text{ present after heating}}{H_2O_2 \text{ present before heating}} \right] \times 100\%$$

In this test the peroxide solution is heated to 100° C. for a period of 24 hours. After returning to the preheating temperature the "after heating" peroxide amount is measured.

This solution is now suitable to disinfect all types of soft contact lens and rigid gas permeable contact lens polymers.

EXAMPLE 2

0.8655 g of NaCl, 0.0622 g of anhydrous, dibasic sodium phosphate, 0.0072 g of monobasic sodium phosphate monohydrate, 0.020 g of Dequest® 2010, and 0.030 g of glycerine are dissolved in 80 ml of purified deionized water (conductivity 0.5 umho). To this solution is added 10 ml of Fisher Chemical pure grade 30% hydrogen peroxide. Water is used to bring the solution to 100 ml, and the pH is adjusted to about 6.5 using HCl or NaOH as needed.

Hot stability of the formulation is over 95%. Disinfection of the polymer materials in Example 1 with this solution left no hazy or milky film.

EXAMPLE 3

Example 2 is repeated using contaminated deionized water (conductivity 1 umho). The same results as in Example 2 are achieved.

EXAMPLE 4

Example 3 is repeated using contaminated deionized water having a conductivity of 2 umho. The same results as in Example 3 are achieved.

EXAMPLE 5

Example 3 is repeated but omitting the glycerine. Hot stability of the formulation drops to 92%.

EXAMPLE 6

Example 4 is repeated but omitting the glycerine. Hot stability of this formulation drops to 90%.

EXAMPLE 7

Example 2 is repeated using 0.05 g glycerin instead of 0.02 g Dequest® 2010 and 0.03 g glycerine. Hot stability is 85%.

EXAMPLE 8

Example 7 is repeated using contaminated water (conductivity 1.0 umho). Hot stability is 82%.

EXAMPLE 9

Example 7 is repeated using water with a conductivity of 2.0 umho. Hot stability is 78%.

EXAMPLE 10

Example 5 is repeated using 0.03 g Dequest® 2010 instead of 0.02 g and using deionized water (conductivity 0.5 umho). Hot stability is 95%.

We claim:

1. A method of disinfecting a polymeric contact lens comprising contacting said lens with a stabilized hydrogen peroxide solution, said solution having a pH of 5.5–8.0 and comprising a disinfectingly effective amount of hydrogen peroxide; a primary stabilizer which is 1,1-diphosphonic acid-ethanol in an amount of about 50 ppm to about 700 ppm based on the entire solution; a secondary stabilizer which is glycerin in an amount of about 50 ppm to about 1000 ppm based on the entire solution; and water.

2. The method of claim 1 wherein said stabilized hydrogen peroxide solution further comprises at least one of
   (a) a tertiary hydrogen peroxide stabilizer;
   (b) a tonicity builder;
   (c) a viscosity enhancer; and
   (d) a buffer.

3. The method of claim 2 wherein said tertiary stabilizer is selected from water soluble stannate, water soluble phosphate, and amino polycarboxylic acid chelating agent;
   said tonicity builder is selected from alkali metal halides, phosphates, hydrogen phosphates, and borates; said viscosity enhancer is selected from polyvinyl alcohol and hydroxyethylcellulose; said buffer is selected from alkali metal phosphate, alkali metal borate, and alkali metal pyruvate each alone or in combination with their respective acidic forms.

4. The method of claim 1 wherein said stabilized hydrogen peroxide solution has a tonicity of about 390 to about 1,350 milliosmoles, before decomposition of said hydrogen peroxide and about 250 milliosmoles to about 350 milliosmoles after said hydrogen peroxide is fully decomposed.

5. The method of claim 1 wherein said stabilized hydrogen peroxide solution has a viscosity of up to 1000 cps.

6. the method of clim 1 wherein said contacting step takes place for at least 10 minutes.

7. The method of claim 6 further comprising decomposing said hydrogen peroxide after said contacting step.

8. The method of claim 7 wherein said stabilized hydrogen peroxide solution, after said decomposing step is substantially isotonic.

9. The method of claim 7 wherein said decomposing step is carried out with an agent which is compatible with the ocular environment.

* * * * *